United States Patent
Cao (10) Patent No.: US 7,179,290 B2
(45) Date of Patent: Feb. 20, 2007

(54) FLEXIBLE HEART VALVE

(75) Inventor: Dongbu Cao, Parma, OH (US)

(73) Assignee: Edwards Lifesciences, Irvine, CA (US)

( * ) Notice: Subject to any disclaimer, the term of this patent is extended or adjusted under 35 U.S.C. 154(b) by 281 days.

(21) Appl. No.: 10/977,409

(22) Filed: Oct. 28, 2004

(65) Prior Publication Data

US 2005/0096739 A1   May 5, 2005

Related U.S. Application Data

(60) Continuation of application No. 10/245,000, filed on Sep. 17, 2002, now abandoned, which is a division of application No. 09/668,660, filed on Sep. 22, 2000, now Pat. No. 6,461,382.

(51) Int. Cl.
*A61F 2/06* (2006.01)

(52) U.S. Cl. ................. 623/2.19; 623/2.17

(58) Field of Classification Search ........... 623/2.17, 623/2.19
See application file for complete search history.

(56) References Cited

U.S. PATENT DOCUMENTS

| | | |
|---|---|---|
| 3,197,788 A | 8/1965 | Segger |
| 3,714,671 A | 2/1973 | Edwards et al. |
| 3,755,823 A | 9/1973 | Hancock |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,343,048 A | 8/1982 | Ross et al. |
| 4,388,735 A | 6/1983 | Ionescu et al. |
| 4,451,936 A | 6/1984 | Carpentier et al. |
| 4,470,157 A | 9/1984 | Love |
| 4,501,030 A | 2/1985 | Lane |
| 4,626,255 A | 12/1986 | Reichart et al. |
| 4,725,274 A | 2/1988 | Lane et al. |
| 4,778,461 A | 10/1988 | Pietsch et al. |
| 4,851,000 A | 7/1989 | Gupta |
| 5,037,434 A | 8/1991 | Lane |

(Continued)

FOREIGN PATENT DOCUMENTS

EP   0 084 395 B1   8/1986

(Continued)

OTHER PUBLICATIONS

Bernhard, et al., "A 'Semi-Supported' Porcine Xenograft—Description and First Clinical Use" Thorac. Cardiovasc. Surgeon 37 (1989) pp. 313-315.

(Continued)

*Primary Examiner*—Tom Barrett
(74) *Attorney, Agent, or Firm*—Rajiv Yaday (57) ABSTRACT

A flexible prosthetic tissue-type heart valve having commissures that are substantially decoupled from a cusp support structure. The valve includes three leaflets having arcuate cusp edges and opposed concave shaped free edges, with outwardly-directed attachment tabs therebetween. A cusp support structure in either one or more pieces attaches to the leaflet cusp edges. Three commissures are each formed partly with an axially-extending insert member to which two adjacent leaflet tabs attach. An inverted V-shaped clip maintains close contact between the adjacent leaflet tabs and provides a stress-relieving clamping action in conjunction with the insert member. The insert member attaches about its lower end to base sections of the cusp support structure, or to an intermediate sewing ring, so that the commissures may pivot about the cusp support structure.

18 Claims, 7 Drawing Sheets

U.S. PATENT DOCUMENTS

| | | |
|---|---|---|
| 5,147,391 A | 9/1992 | Lane |
| 5,163,953 A | 11/1992 | Vince |
| 5,163,955 A | 11/1992 | Love et al. |
| 5,258,023 A | 11/1993 | Reger |
| 5,411,552 A | 5/1995 | Andersen et al. |
| 5,449,384 A | 9/1995 | Johnson |
| 5,489,297 A | 2/1996 | Duran |
| 5,489,298 A | 2/1996 | Love et al. |
| 5,500,016 A | 3/1996 | Fisher |
| 5,549,665 A | 8/1996 | Vesely et al. |
| 5,554,185 A | 9/1996 | Block et al. |
| 5,697,382 A | 12/1997 | Love et al. |
| 5,716,417 A | 2/1998 | Girard et al. |
| 5,728,152 A | 3/1998 | Mirsch, II et al. |
| 5,855,601 A | 1/1999 | Bessler et al. |
| 5,861,028 A | 1/1999 | Angell |
| 5,910,170 A | 6/1999 | Reimink et al. |
| 5,928,281 A | 7/1999 | Huynh et al. |
| 5,935,163 A | 8/1999 | Gabbay |
| 6,338,740 B1 | 1/2002 | Carpentier |
| 6,682,559 B2 | 1/2004 | Myers et al. |

FOREIGN PATENT DOCUMENTS

| | | |
|---|---|---|
| EP | 0 515 324 B1 | 12/1996 |
| GB | 2 279 134 A | 12/1994 |
| RU | 1806696 A1 | 4/1993 |
| WO | 90/11738 | 10/1990 |
| WO | 92/12690 | 8/1992 |
| WO | 93/18721 | 9/1993 |
| WO | 95/28899 | 11/1995 |
| WO | 97/46177 | 12/1997 |
| WO | 98/43556 | 10/1998 |
| WO | 00/00107 | 1/2000 |

OTHER PUBLICATIONS

Jansen, et al., "New J-3 Flexible-Leaflet Polyurethane Heart Valve Prosthesis With Improved Hydrodynamic Performance" The International Journal of Artificial Organs, vol. 14, No. 10 (1991) pp. 655-660.

Krucinski, et al., "Numerical Simulation of Leaflet Flexure in Bioprosthetic Valves Mounted on Rigid and Expansile Stents" J. Biomechanics vol. 26, No. 8 (1993) pp. 929-943.

FLEXIBLE HEART VALVE

RELATED APPLICATIONS

The present application is a continuation of application Ser. No. 10/245,000, filed on Sep. 17, 2002, now abandoned, which is a divisional of application Ser. No. 09/668,660, filed on Sep. 22, 2000, now U.S. Pat. No. 6,641,382 B1.

FIELD OF THE INVENTION

The present invention relates generally to medical devices and particularly to flexible tissue-type heart valve prostheses designed to attach along the valve annulus and adjacent anatomical wall structure.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment. Importantly, the wireform provides continuous support for each leaflet along the cusp region so as to better simulate the natural support structure. However, the tissue material tends to calcify after the long term implantation. That is, calcium compound accumulates in the tissue leaflets, eventually making them stiff. The tissue leaflet area along the wireform is especially susceptible to the calcification because of the high bending stresses imposed at that interface.

Many prior art stented valves are relatively rigid, typically containing an annular metal or plastic stent ring that provides internal support for an outer sewing ring and the wireform-mounted valve cusps and commissures. This design also provides a basic structure to facilitate valve assembly, which is hand made by highly skilled workers. Although this type of valve has been proven effective, some researchers assert that it excessively occludes the natural orifice area, and thus reduces potential blood flow therethrough. Although stentless valves generally provide greater orifice area, they do not have the advantage of the reliable leaflet support structure of stented valves. Moreover, a stentless valve is more difficult to make, and the implantation of such a device requires much more skill and experience of the cardiac surgeon. Only a few heart centers in the United States are able to perform such a procedure and thus the use of stentless valves is restricted.

More flexible stented valves have been proposed, including U.S. Pat. No. 5,549,665 to Vesely, et al. In the Vesely patent, the valve stent commissures may attach to the ascending aorta and may pivot outward for the purpose of reducing localized stresses in the leaflets. The stent commissures are prevented by stops from inward pivoting to ensure proper valve functioning. However, the stent structure appears to be relatively complex, with numerous interior surfaces, thus raising concerns of thromboembolisms and even component failure.

In view of the foregoing, it is evident that an improved flexible valve that addresses the apparent deficiencies in existing heart valves is necessary and desired. In particular, there is a need for a bioprosthetic valve that provides a large orifice opening and has a dimensionally stable stent to facilitate the valve assembly and implantation.

SUMMARY OF THE INVENTION

This invention details a partially stented valve design. The stent is to be completed by the natural aortic root when the valve is implanted. The final valve conforms to the movement of the natural aortic root and therefore provides a larger orifice area like a stentless valve. The valve, however, includes a stent structure that will facilitate the valve assembly and implantation procedures. The movement of the stent structure and leaflet shape also helps to reduce stress concentration in the valve leaflet.

In one embodiment, the present invention provides a heart valve for implantation in an annulus of a heart having commissures on an outflow end adapted to move in conformity with an anatomical wall structure adjacent the annulus. The heart valve comprises three leaflets made of a biocompatible and compliant material, each leaflet having a rounded cusp edge opposite a free edge, and a pair of generally oppositely-directed tabs separating the cusp edge and free edge. A cusp support structure generally defines a ring and a valve axis and has three rounded sections each adapted to conform to the cusp edge of the leaflets. The cusp edge of each leaflet is attached to a different rounded section of the cusp support structure so that the three leaflets are arranged generally evenly about the valve axis, the attached leaflet cusp edges and rounded sections together defining valve cusps curving toward an inflow end of the valve. Three valve commissure posts disposed between the valve cusps project generally axially toward an outflow end of the valve. The commissure posts are defined by two adjacent leaflet tabs, a generally axially extending insert member, and an inverted V-shaped clip positioned radially inward from the insert member. The adjacent leaflet tabs are juxtaposed to extend radially outward with respect to the axis through the inverted V-shaped clip and are wrapped around and secured to the insert member, an inflow end of each commissure post is generally pivotally coupled with respect to the cusp support structure so as to permit both radially inward and outward movement thereof, the valve commissure posts being attachable to the anatomical wall structure. Finally, a sewing band shaped to follow the valve cusps and being attached therealong provides a platform for implanting the heart valve such that the valve cusps are attachable adjacent the annulus or in the supraannular position (i.e., just above the annulus).

In another aspect of the invention, an aortic heart valve adapted to have reduced vibration-related strain is provided, comprising three leaflets each having arcuate cusp edges on their inflow ends, free edges on the outflow ends, and two side tabs. Three cusp supports each attach to the cusp edge of one of the leaflets to define valve cusps, the cusps being disposed generally in a circle about a valve axis at an inflow end of the valve. Three generally axially extending commissure posts are disposed in between the valve cusps around the circle and extend toward an outflow end of the valve. The commissure posts are defined by a relatively rigid insert and adjacent tabs of two leaflets attached thereto. The inserts are structurally separate from the three cusp supports but coupled thereto at an end closest to the cusp supports to enable radial pivoting of the outflow end of the commissure posts. Finally, a sewing band shaped to follow the valve cusps and attached therealong is provided. The sewing band and inserts providing a platform for implanting the aortic heart valve such that the valve cusps are attachable adjacent the annulus, and the inserts are attachable to the ascending aorta. In this manner, the commissure posts are freely moveable with respect to the valve cusps so as to generally pivot radially in and out in conjunction with movement of the ascending aorta during the repetitive cycles of systole and diastole such that the heart valve is dynamically coupled to the damping characteristics of the ascending aorta.

In a further aspect of the invention, a tissue-type heart valve adapted to have reduced stress risers in the leaflets, comprises three leaflets each having arcuate cusp edges on their inflow ends, free edges on the outflow ends, and two side tabs, the free edges extending between the side tabs in a concave fashion. The valve may include commissure posts to which adjacent leaflet tabs attach, each post including an insert around which the leaflet tabs wrap. The valve further may include a cusp support structure attached to the cusps of each leaflet, wherein the insert is pivotally coupled to the cusp support structure. Desirably, a sewing band for attachment to a valve annulus that surrounds the cusp support structure and is truncated in the region of the inserts to permit direct attachment of the commissure posts to an anatomical wall structure adjacent the annulus. Each leaflet free edge further may include a region that is above a line extending between the middle of the free edge and the side tabs so that the region is not placed in direct tension during closure of the valve. The region is preferably generally triangular and culminates in an apex, and a concave filet may exist between the apex and the side tab.

A further understanding of the nature advantages of the invention will become apparent by reference to the remaining portions of the specification and drawings.

DESCRIPTION OF THE PREFERRED EMBODIMENTS

The following detailed description, and the figures to which it refers, are provided for the purpose of describing examples and specific embodiments of the invention only and are not intended to exhaustively describe all possible examples and embodiments of the invention. Identical elements and features are given the same reference number as appropriate for purposes of describing the various embodiments of the present invention.

Figure 1:
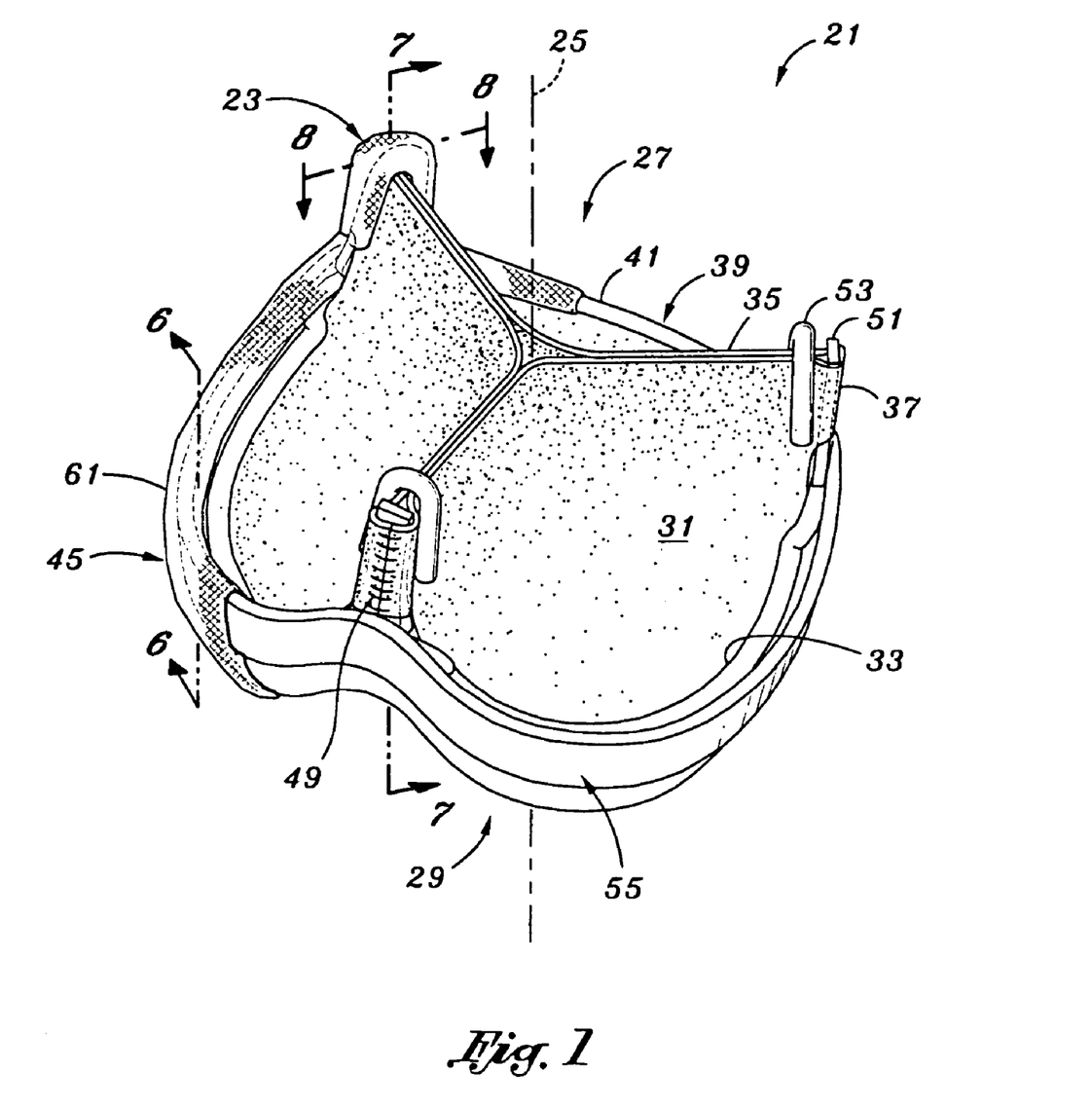
FIG. 1 is an assembled perspective view of the flexible heart valve of the present invention.
Figures 2, 2A:
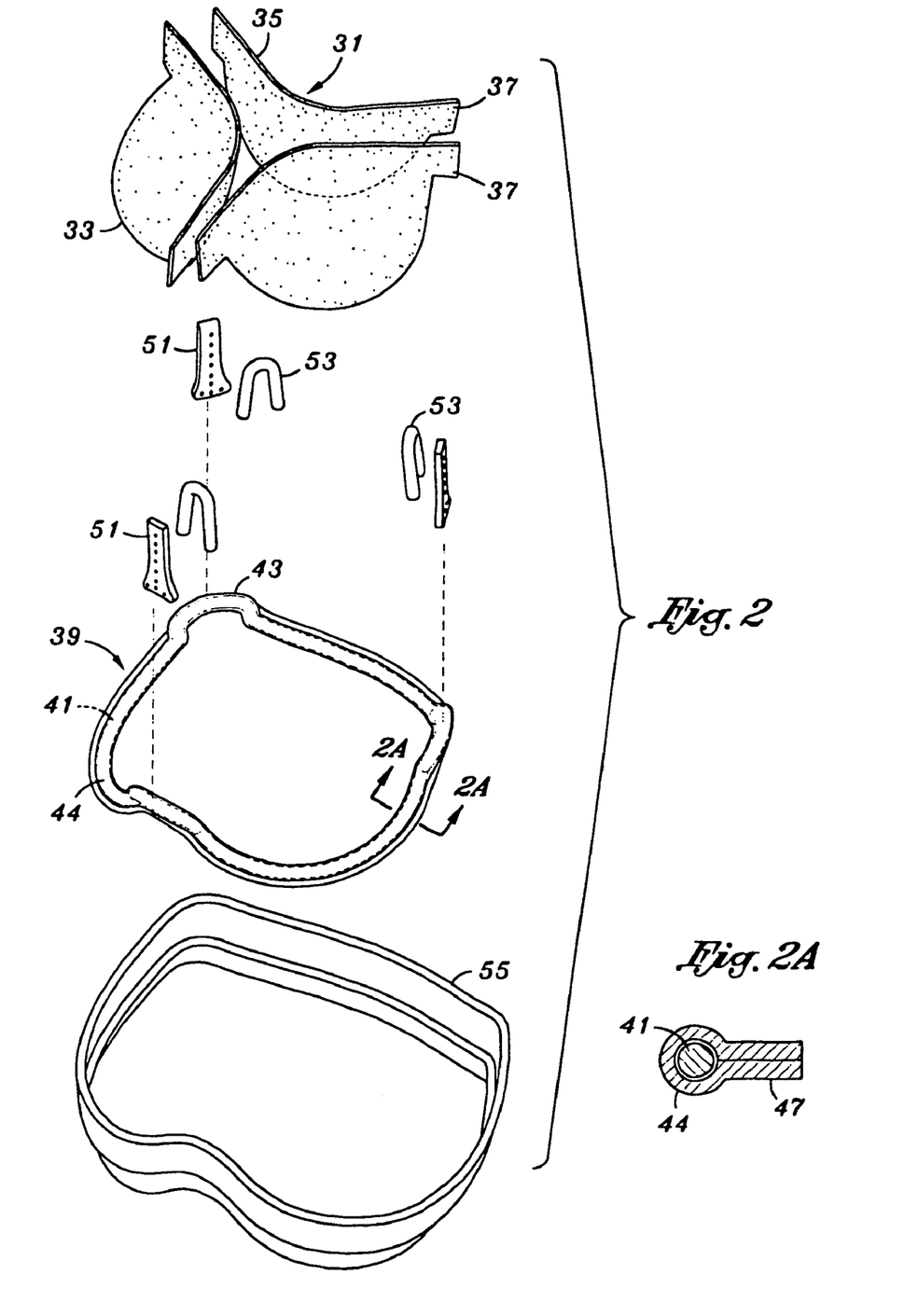
FIG. 2 is an exploded perspective view of the heart valve of FIG. 1.
FIG. 2A is a sectional view through a cusp support structure of the heart valve of FIG. 1, taken through line 2A—2A of FIG. 2.
Figure 13A:
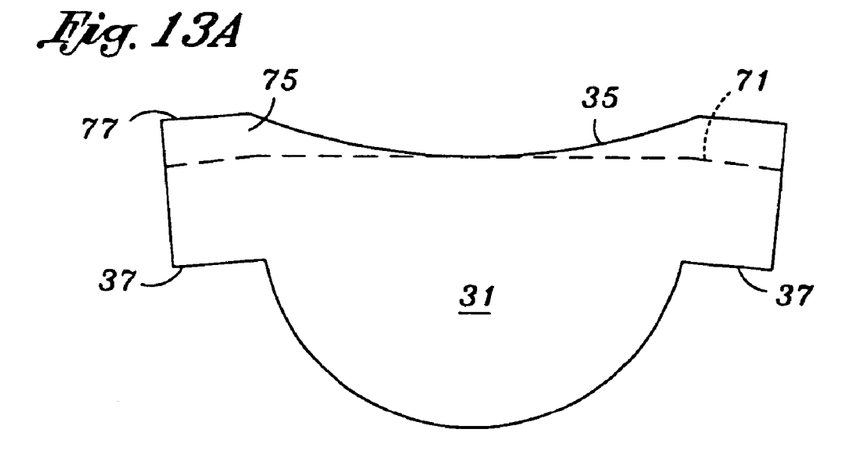
FIG. 13A is a plan view of a first embodiment of a valve leaflet for use in the flexible valve of the present invention.
Figure 13B:
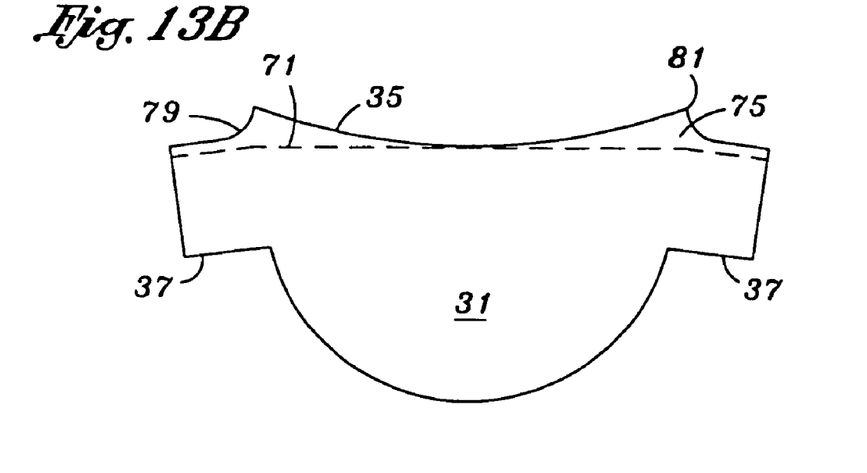
FIG. 13B is a plan view of a second embodiment of a valve leaflet for use in the flexible valve of the present invention.

Referring now to FIGS. 1 and 2, a replacement tissue type heart valve 21 of the present invention for implantation in an annulus of a heart is constructed about a valve axis 25 that defines an outflow end 27 and an inflow end 29. The valve includes commissures 23 directed to the outflow end and adapted to move in conformity with an anatomical wall structure adjacent the annulus of the heart. Although the valve 21 of the present invention is particularly suitable for implantation at the aortic valve position, it may also function adequately in other valve positions. The valve has three leaflets 31 made of a biocompatible compliant material, each of which has a rounded cusp edge 33 opposite a free edge 35 and a pair of generally oppositely-directed tabs 37 separating the cusp edge and the free edge. The specific shapes of alternative embodiments of the leaflets 31 of the present invention are shown in FIGS. 13A and 13B, and will be described in more detail below.

A valve cusp support structure 39 is provided, generally defining a ring comprised of three rounded sections 41 connected by commissure base sections 43. The entire support structure 39, including the rounded sections 41 and base sections 43, is covered with a fabric sleeve 44. Each of the rounded sections 41 conforms and attaches to a rounded cusp edge 33 of a leaflet via the fabric sleeve 44. As seen in the cross-section of FIG. 2A, the fabric sleeve 44 exhibits a flap 47 formed by juxtaposed free ends of the fabric material to which the cusp edge 33 of each leaflet 31 attaches, such as with sutures (not shown). The cusp edge 33 of each leaflet 31 is attached to a different rounded section 41 of the cusp support structure 39 so that the three leaflets 31 are arranged generally evenly distributed 120° apart about the valve axis 25. The attached leaflet cusp edges 33 and rounded sections 41 together define valve cusps 45 concavely curved toward the inflow end 29 of the valve.

The three valve commissure posts 23 are disposed between the valve cusps 45 and project generally axially toward the outflow end 27 of the valve. The commissure posts 23 include a generally axially extending insert member 51 attached to two adjoining leaflet tabs 37, here shown sutured together at butt joint 49. Alternatively, as will be described below with respect to FIG. 8, the leaflet tabs 37 may overlap and can be mutually attached via stitching through holes in the insert member 51. The leaflet free edges 35 coapt in the middle of the valve and the free edges of each two adjacent leaflets are juxtaposed so that the tabs 37 extend radially outwardly from the valve axis 25 through an inverted V-shaped clip 53 positioned radially inward from the insert member 51. Each insert member 51 is sutured to the cover fabric of the commissure base section 43 so as to permit both radially inward and outward movement of the outflow end of the commissure posts. This generally pivoting attachment (shown by arrow 54 in FIG. 7) may be accomplished in a number of ways, several of which are disclosed herein, and to some extent decouples the radial movement of the valve commissures 23 from its cusps 45.

A sewing band 55 shaped to follow the valve cusps 45 and to an extent the valve commissures 23 provides a platform for attaching the heart valve to vestigial heart tissue, such as the aortic annulus or aortic root tissue. As partially seen in FIG. 1, the sewing band 55 is encompassed within a fabric cover 61 (shown partially cutaway). The valve cusps 45 are attachable adjacent the annulus with the valve commissures 23 attachable to the adjacent anatomical wall structure itself. Consequently, when implanted, structural support for each valve commissure 23 is provided by the native aorta, through the V-shaped clip 53 and insert member 51. In the preferred embodiment, the valve 21 is attached to the root tissue that comprised part of the native aortic heart valve. Attachment in this manner allows the replacement valve to more freely move and thus exhibit greater flexibility to match the blood flow capacity of the native aortic heart valve. Moreover, this biomechanical coupling provides natural tissue damping to help suppress excessive vibrations within the valve 21 during its rapid closing.

Referring to the exploded view of FIG. 2, the component parts of the invention will be described in more detail. As mentioned, the three tissue leaflets 31 have a tab section 37, a rounded cusp edge 33 and a free edge 35. The insert members 51 rest on the relatively rigid fabric-covered commissure base sections 43 (in this embodiment a rod-like element), and are attached thereto. For instance, sutures are passed through each insert member 51 and around the associated commissure base section to allow the insert member to move both radially inwardly and radially outwardly. This allows the finished commissure posts (FIGS. 7 and 8) to move both radially inwardly and radially outwardly. V-clips 53 and sewing band 55 are shown in their relative orientation in FIG. 2 without connecting structure, to be described below.

Figure 3:
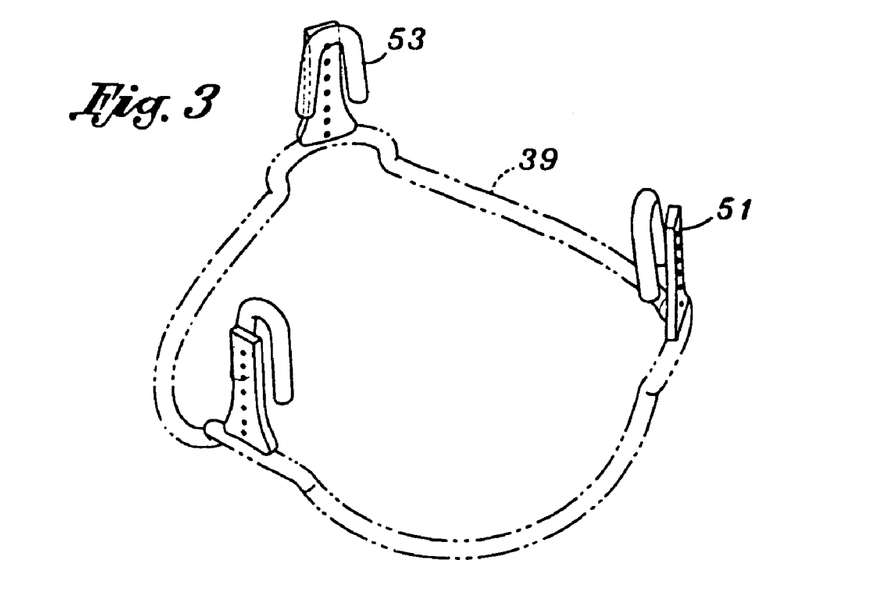
FIG. 3 is a perspective view of components of the three commissures of the heart valve of FIG. 1 positioned with respect to the cusp support structure shown in phantom.
Figures 4A, 4B:
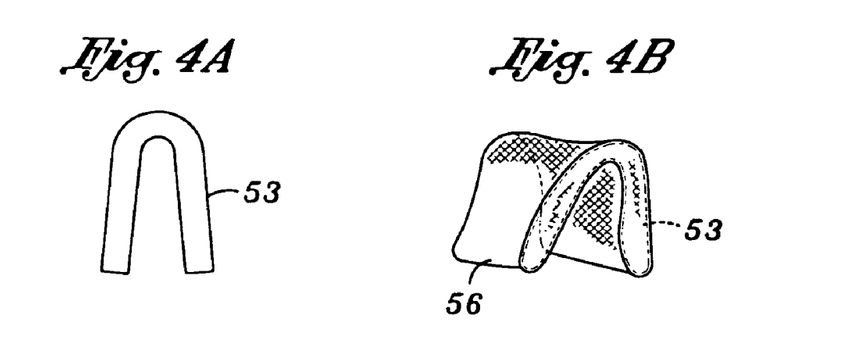
FIG. 4A is an elevational view of an inverted V-shaped clip forming a portion of each of the valve commissures.
FIG. 4B is a perspective view of the inverted V-shaped clip of FIG. 4A showing a fabric-covering thereon.
Figure 5A:
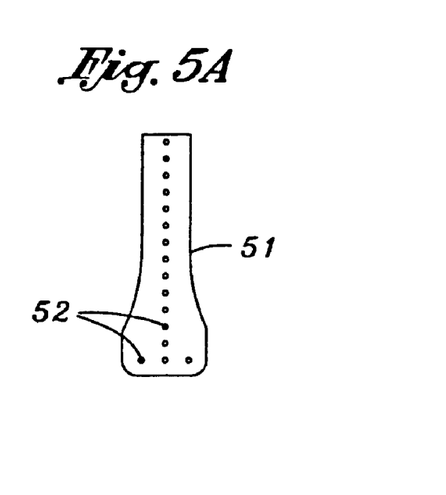
FIGS. 5A and 5B are front and side elevational views, respectively, of an insert member that forms another portion of each of the valve commissures.
Figure 5B:
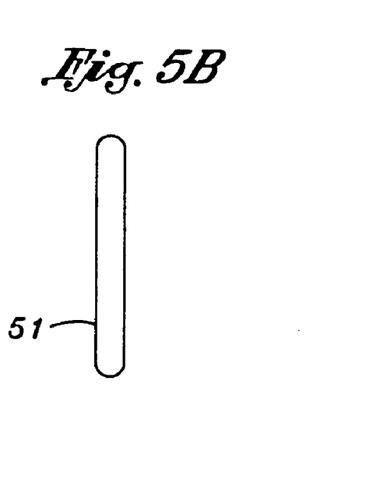
Figures 6, 7, 8:
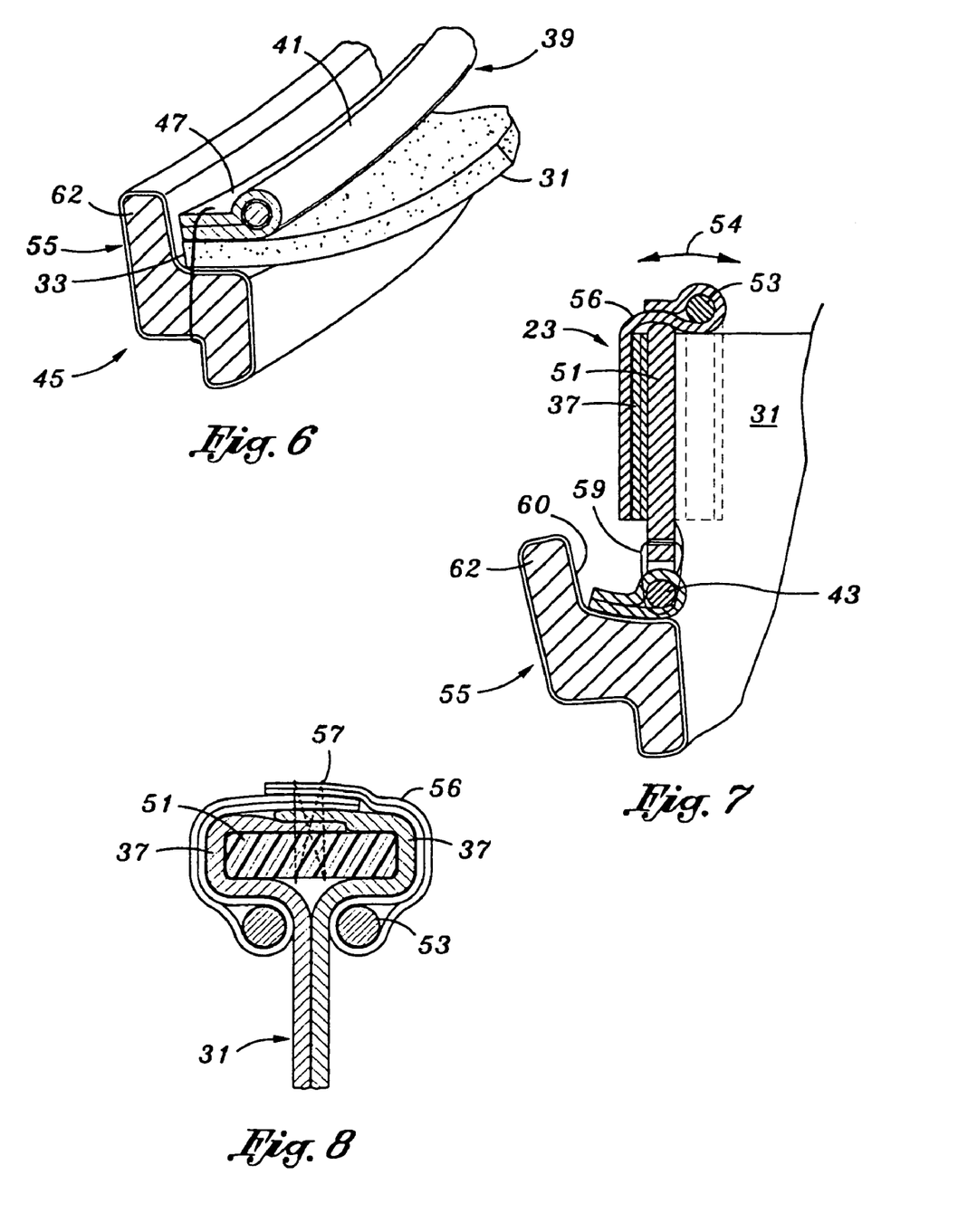
FIG. 6 is a vertical sectional view through a valve cusp taken along line 6—6 of FIG. 1.
FIG. 7 is a vertical sectional view through a valve commissure taken along line 7—7 of FIG. 1.
FIG. 8 is a horizontal sectional view through a valve commissure taken along line 8—8 of FIG. 1.

FIG. 3 shows the relative orientation of the V-shaped clip 53 (shown isolated in FIGS. 4A and 4B), and the insert member 51 on the cusp support structure 39 (shown in phantom) when they are assembled. The cusp support structure 39 may be formed in a generally annular or ring like shape. The V-shaped clips 53, seen in FIGS. 4A and 4B, cinch the tissue leaflet free edges 35 to the commissure posts, as indicated in FIG. 8. In a preferred embodiment, a shroud-like fabric cover 56 is provided around each V-shaped clip 53 to facilitate attachment to the adjacent valve components. FIGS. 5A and 5B show front and side views of the insert member 51 having a series of through holes 52.

FIG. 6 is a sectional view taken along the 6—6 line of FIG. 1, showing the attachment of the rounded cusp edge 33 of the tissue leaflet, the rounded section 41 of the cusp support structure 39 and the sewing band 55. The three pieces are sutured or otherwise attached together in this manner at least along the valve cusps 45 shown in FIG. 1.

FIG. 7 illustrates one embodiment of the attachment of the insert member 51 to the commissure base section 43 of the cusp support structure utilizing a suture 59 looped through holes 52 in the insert member and then around the base section. The insert 51 is thereby freely attached to the commissure base section 43 to allow its outflow end to move radially inwardly and outwardly, as indicated by arrow 54. The sewing band 55 is not connected to the insert member 51 but instead receives each commissure base section 43 in a groove portion 60. An outflow flange 62 stops short of the insert members 51 and the V-shaped clip 53. That is, the flange 62 of the sewing band 55 is axially truncated so as not to extend fully up each commissure 23. In this arrangement, the valve commissures 23 are exposed to the aortic wall so that they can be sutured directly thereto.

In an alternative embodiment, the commissure base sections 43 of the cusp support structure 39 are omitted to result in three separate cusp supports that attach to the sewing ring 55, such as seen in FIG. 6. In such an alternative, each insert member 51 will rest directly on the sewing ring, and its inflow end may be sutured to the sewing ring.

FIGS. 7 and 8 illustrate the complete structure of the commissures 23 wherein adjacent leaflet tabs 37 wrapped around the insert member 51 and are sutured together on the radially outward side of the insert member. Fabric-covered V-shaped clip 53 is placed over adjoining leaflet tabs 37 and the fabric cover 56 includes a shroud long enough to wrap around the insert member 51. After the V-shaped clip 53 is placed over the leaflets at the commissure 23, the shroud of the fabric cover 56 is pulled down to cover the outward side of the insert member 51 and the leaflet tabs 37, and the free ends thereof are wrapped around the insert member 51 and sutured together (using sutures, not shown). Also, the fabric cover 56 may be sutured to the insert member 51 and leaflet tabs 37 through the aligned holes at the insert member 51 for additional support, such as by using a stitch 57. The V-shaped clips 53 are desirably formed of a flexible material that flexes apart during an opening cycle of the valve wherein fluid flow through the valve causes the free edges 35 of adjacent leaflet tabs 37 to separate.

In this manner the leaflet tabs 37 are anchored to the commissures 23 by the clamping action between the insert 51 and the V-shaped clip 53. That is, each leaflet 31 experiences radially inward forces upon closing of the valve 21, which also tends to pull the insert member 51 inwardly. Because the fabric cover 56 attaches to the surrounding native aorta, and thus the V-shaped clip 53 is retained thereby, this radially inward movement of the insert member 51 clamps the leaflet tabs 37 between the insert member and the clip. This anchoring prevents the sutures, such as suture 57, from being directly stressed and pulled apart through the leaflet material when the valve closes by blood flow during diastole. Further, this anchoring prevents any tissue stitches from being exposing to direct hemodynamic loading and thus prevent stress concentration.

Figures 9, 10, 11:
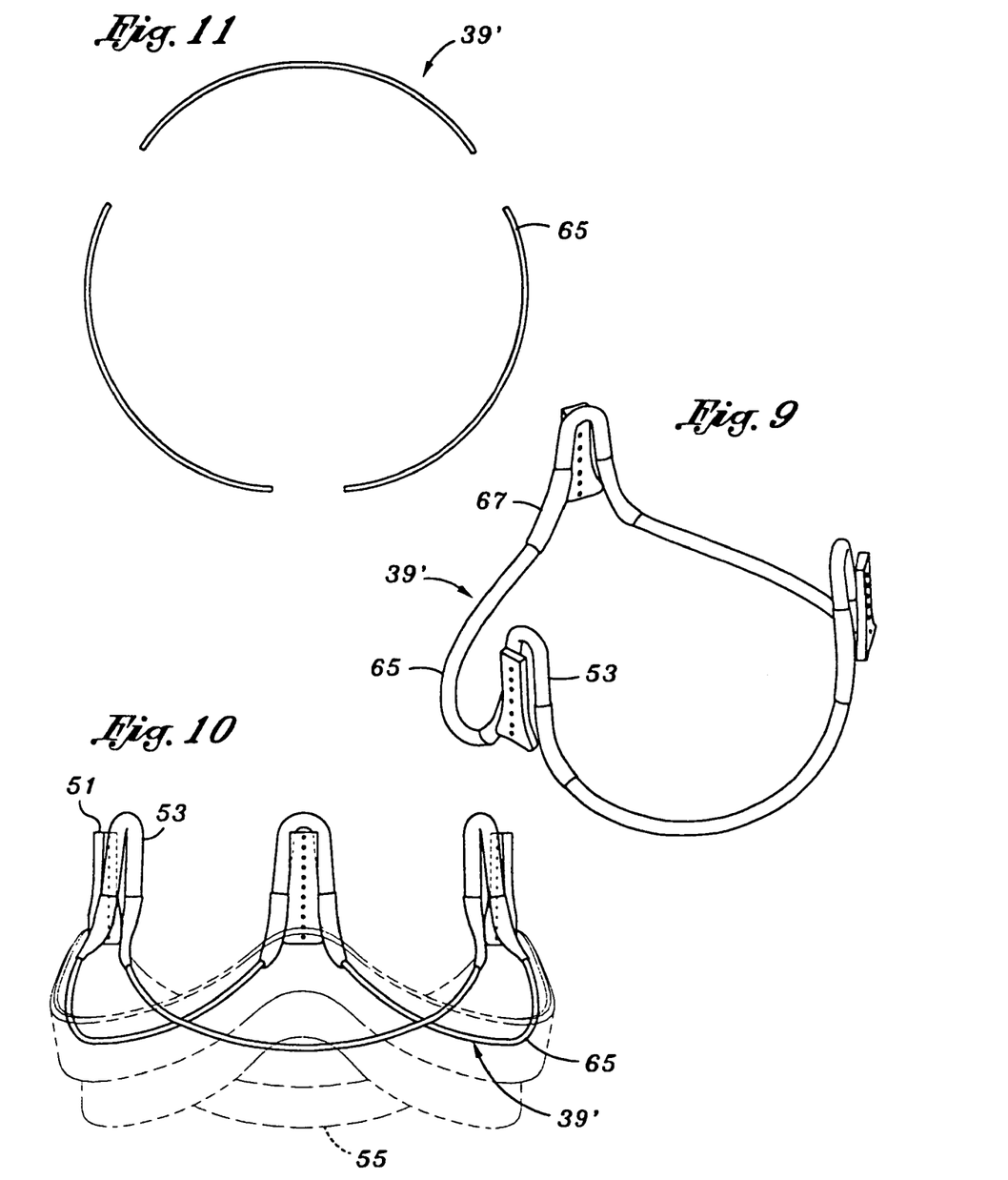
FIG. 9 is a perspective view of an alternative three-piece cusp support structure for the flexible valve of the present invention, also showing the positioning of valve commissure components.
FIG. 10 is an elevational view of the alternative cusp support structure and valve commissure components of FIG. 9, further illustrating a sewing band in phantom.
FIG. 11 is a top plan view of the alternative three-piece cusp support structure of FIG. 9.

FIGS. 9–11 show an alternative embodiment of the invention wherein a cusp support structure 39' comprises three separate rounded sections 65 each respectively supporting the rounded cusp edge 33 of a leaflet. Adjacent rounded sections may be interconnected with separate connector sections 67 and intermediate V-shaped clips 53. The connector sections 67 may be made of a highly compliant material, for example a fabric, silicone or other elastomer to allow the rounded sections to move with respect to one another and more flexibly accommodate static or dynamic distortions in the shape of the native heart tissue. As before, insert 51 and V-shaped clips 53 are shown in the relative orientation as before to form the valve commissures to which the leaflet tabs (not shown) attach.

The three separate rounded sections 65 may be relatively rigid rod-like elements made of biocompatible metals or polymers. Alternatively, the rounded sections 65 may be made of a pre-formed biocompatible fabric having a radially outward tab to which the cusp edge of a leaflet attaches. In the latter case, the rounded sections 65 are less rigid than a metal or polymer material, but provide sufficient stiffness to facilitate fabrication and implantation.

FIG. 10 shows the use of the scalloped-shaped cusp support structure of FIG. 9 with a corresponding scalloped shaped sewing band 55. As is known, this scalloped shape more readily accommodates use of the sewing band as a platform to suture the sewing band to aortic root tissue, which is likewise scalloped. In this embodiment the sewing band is sutured directly to the valve annulus, with the commissure posts attached to the aortic wall to allow the leaflets to fluctuate radially inwardly and outwardly in a more natural manner. The inserts 51 are desirably directly sutured to the sewing band 55, and thus there is no direct connection between the inserts 51 and the cusp support structure 39', and the valve commissures remain free to move inwardly and outwardly.

Figure 12:
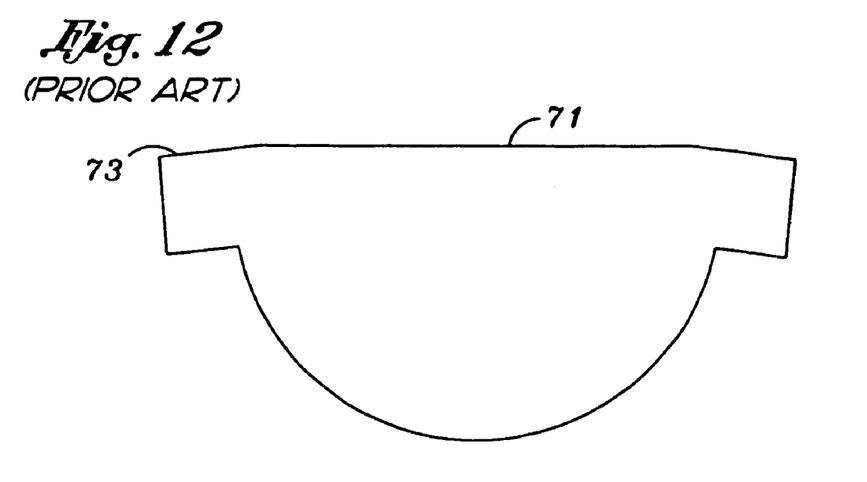
FIG. 12 is a plan view of a valve leaflet of the prior art.

FIG. 12 shows a leaflet of prior art tissue-type replacement heart valves. The free edge 71 of prior art leaflets generally extends straight across between the opposed tabs 73.

For the present invention, the tissue leaflets should be configured as shown in either FIG. 13A or 13B for reduced stress in the highly flexible valves. Leaflet free edge 35 between the tabs 37 is concave with either one or more curvatures (i.e., simple or complex curves). The outline of the free edge 71 of a prior art leaflet is shown in phantom superimposed over the new leaflets. As can be seen, extra material 75 is provided at the leaflet tabs 37 to accommodate the additional stresses imposed upon the leaflets from the increased radially inward and outward movement of the valve commissures. That is, the leaflet tabs 37 are axially higher than the middle portions of the free edges. In the embodiment of FIG. 13A, the leaflet tabs 37 continue outward a straight edge 77 from the concave free edge 35. In the embodiment of FIG. 13B, a concave transition filet 79 is provided from an apex 81 of the free edge 35 to reduce the height of the tabs at the valve commissures from that shown in FIG. 13A. The triangular region near the apex 81 is not placed in direct tension from valve closure forces, and helps reduce stress concentrations in the integrally connected regions that are in direct tension.

Figure 14:
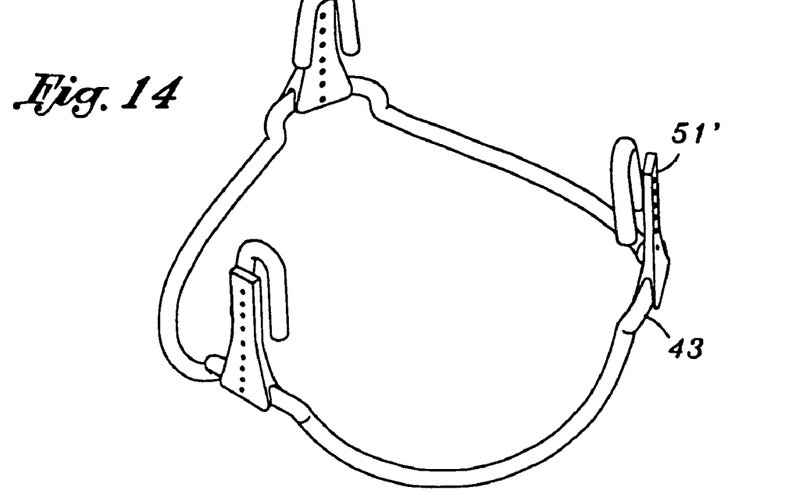
FIG. 14 is a perspective view of a cusp support structure as seen in FIG. 2, and alternative commissure components for use in a flexible valve of the present invention.
Figure 16A:
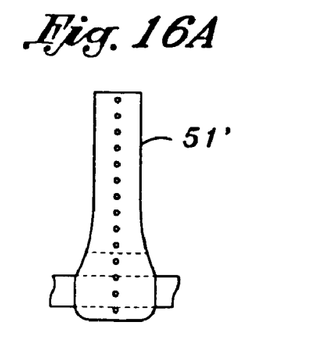
FIGS. 16A and 16B are front and side elevational views, respectively, of an insert member of the valve of FIG. 14 coupled to a cusp support structure.
Figure 16B:
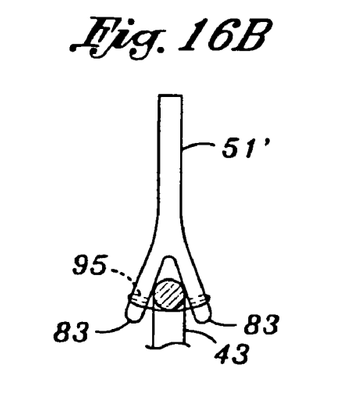

Referring now to FIG. 14, in an alternative embodiment, the lower end of each insert member 51' bifurcates to straddle the commissure base section 43. The lower end of the insert member 51 thus straddles the base section 43 to facilitate radially inward and outward pivoting and reduces the tendency to slip off of the commissure base section. The bifurcation ends 83 seen in FIGS. 16A and 16B are disposed on either side of the commissure base section 43 and are secured thereto using a suture 85.

Figure 15:
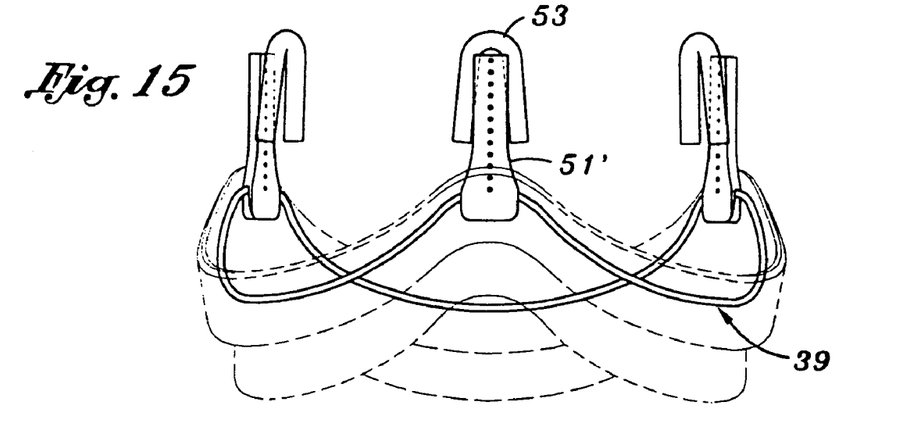
FIG. 15 is an elevational view of the assembly of FIG. 14, further illustrating a sewing band in phantom.

FIG. 14 shows the relative orientation of the three valve commissure posts, each including a V-shaped clip 53, an insert member 51' and the cusp support structure 39, when they are assembled. FIG. 15 shows the embodiment of FIG. 14 further including the sewing band 55 in phantom.

In the various valves of the present invention, structural support from the cusp supports is provided to facilitate fabrication and implantation. The commissures remain flexibly coupled to the rest of the valve to enable aortic wall mounting, and dynamic coupling with the natural tissue. A concave free edge of the leaflet, preferably with an apex region that is not placed in direct tension, further prevents stress risers in the leaflets, and contributes to durability.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A heart valve for implantation in an annulus of a heart having commissures on an outflow end adapted to move in conformity with an anatomical wall structure adjacent the annulus, the heart valve comprising:

three leaflets made of a biocompatible and compliant material, each leaflet having a rounded cusp edge opposite a free edge, and a pair of generally oppositely-directed tabs separating the cusp edge and free edge;

a cusp support structure generally defining a ring and a valve axis and having three separate rounded pieces arranged generally evenly about the valve axis to define the ring each rounded piece adapted to conform to the cusp edge of one of the leaflets, the cusp edge of each leaflet being attached to a different rounded piece of the cusp support structure so that the three leaflets are arranged generally evenly about the valve axis, the attached leaflet cusp edges and rounded pieces together defining valve cusps curving toward an inflow end of the valve; and three valve commissure posts disposed between the valve cusps and projecting generally axially toward an outflow end of the valve, the commissure posts being defined by a generally axially extending insert member, and an inverted V-shaped clip positioned radially inward from the insert member, tabs from each two adjacent leaflets being juxtaposed to extend radially outward with respect to the axis through the inverted V-shaped clip and being wrapped around and secured to the insert member, the valve commissure posts being attachable to the anatomical wall structure; and six highly compliant connector sections attached between adjacent ends of the rounded pieces of the cusp support structure and the V-shaped clips to permit pivoting of the valve commissure posts.

2. The heart valve of claim 1, wherein the connector sections are made of fabric.

3. The heart valve of claim 1, wherein the connector sections are made of an elastomer.

4. The heart valve of claim 1, wherein each piece of the cusp support structure comprises a relatively rigid rod-like element having a fabric covering.

5. The heart valve of claim 1, further including a sewing band shaped to follow the valve cusps and being attached therealong, the sewing band providing a platform for implanting the heart valve such that the valve cusps are attachable adjacent the annulus.

6. The heart valve of claim 5, wherein the sewing band attaches to the valve cusps and wherein the inflow end of each commissure post is pivotally attached to a portion of the sewing band that bridges one of three gaps defined between the three separate pieces of the cusp support structure.

7. The heart valve of claim 6, wherein each piece of the cusp support structure is made of a pre-formed biocompatible fabric having a radially outward tab to which the cusp edge of a leaflet attaches.

8. The heart valve of claim 1, wherein each V-shaped clip is formed of a flexible material adapted to flex apart during an open cycle of the valve wherein fluid flow through the valve causes the free edges of adjacent leaflet tabs to separate.

9. The heart valve of claim 8, further including a fabric covering around each V-shaped clip that extends around the associated insert member and permits suture attachment of the clip to the insert.

10. The heart valve of claim 1, wherein the three leaflets each have a concave free edge.

11. A prosthetic aortic heart valve having pivoting commissures, comprising:

three flexible leaflets having cusp edges;

a one piece ring-shaped cusp support structure having three cusp supports that are curved toward the inflow end of the valve and are connected by three commissure base sections, each cusp support being attached to the cusp edge of one of the leaflets to define valve cusps, the valve cusps being disposed generally in a circle about a valve axis at an inflow end of the valve;

three generally axially extending commissure posts disposed in between the valve cusps around the circle and extending toward an outflow end of the valve, the commissure posts each being defined by an insert to which two adjacent leaflets attach, wherein the inserts are structurally separate from the three cusp supports but coupled thereto at an end closest to the cusp supports to enable radial in and out pivoting of the outflow end of the commissure posts relative to the cusp supports;

a sewing band shaped to follow the valve cusps and being attached therealong, the sewing band and inserts providing a platform for implanting the aortic heart valve such that the valve cusps are attachable adjacent the annulus, and the inserts are attachable to the ascending aorta, the commissure posts therefore being freely moveable with respect to the valve cusps so as to generally pivot radially in and out in conjunction with movement of the ascending aorta during the repetitive cycles of systole and diastole such that the heart valve is dynamically coupled to the damping characteristics of the ascending aorta.

12. The heart valve of claim 11, wherein the inflow end of the insert member of each commissure post is bifurcated and straddles the associated commissure base section.

13. The heart valve of claim 11, wherein the cusp support structure comprises a relatively rigid rod-like element having a fabric covering, the commissure posts being attached to the commissure base sections of the cusp support structure using sutures through the fabric covering.

14. The heart valve of claim 11, wherein each flexible leaflet further includes free edges on the outflow ends, and two side tabs, and wherein the side tabs of adjacent leaflets wrap around and are secured to the corresponding insert.

15. The heart valve of claim 14, wherein each of the commissure posts further includes an inverted V-shaped clip positioned radially inward from the insert, the adjacent leaflet tabs being juxtaposed to extend radially outward with respect to the axis through the inverted V-shaped clip and being wrapped around and secured to the insert.

16. The heart valve of claim 15, wherein each V-shaped clip is formed of a flexible material adapted to flex apart during an open cycle of the valve wherein fluid flow through the valve causes the free edges of adjacent leaflet tabs to separate.

17. The heart valve of claim 15, further including a fabric covering around each V-shaped clip that extends around the associated insert and permits suture attachment of the clip to the insert.

18. The heart valve of claim 14, wherein the three leaflets each have a concave free edge.

* * * * *